United States Patent
Ganzoni

(10) Patent No.: US 11,351,066 B2
(45) Date of Patent: Jun. 7, 2022

(54) COMPRESSION GARMENT COMPRISING SPACER FABRIC AND HOOK FASTENER

(71) Applicant: SIGVARIS AG, St. Gallen (CH)

(72) Inventor: Levin Andreas Ganzoni, Zurich (CH)

(73) Assignee: SIGVARIS AG, St. Gallen (CH)

( * ) Notice: Subject to any disclaimer, the term of this patent is extended or adjusted under 35 U.S.C. 154(b) by 579 days.

(21) Appl. No.: 16/332,354

(22) PCT Filed: Sep. 5, 2017

(86) PCT No.: PCT/EP2017/072213
§ 371 (c)(1),
(2) Date: Mar. 12, 2019

(87) PCT Pub. No.: WO2018/054682
PCT Pub. Date: Mar. 29, 2018

(65) Prior Publication Data
US 2019/0216653 A1 Jul. 18, 2019

(30) Foreign Application Priority Data

Sep. 20, 2016 (CH) ........................................ 1223/16

(51) Int. Cl.
*A61F 13/08* (2006.01)
*A61F 5/32* (2006.01)
(Continued)

(52) U.S. Cl.
CPC .............. *A61F 13/085* (2013.01); *A61F 5/32* (2013.01); *A61F 13/064* (2013.01); *A61L 15/14* (2013.01)

(58) Field of Classification Search
CPC .................... A61F 13/08; A61F 13/085; A61F 2013/0028; A61F 13/0273;
(Continued)

(56) References Cited

U.S. PATENT DOCUMENTS 2,687,723 A 8/1954 Stern
3,613,679 A 10/1971 Bijou
(Continued)

FOREIGN PATENT DOCUMENTS

AU 6414174 A 7/1975
AU 2017329457 A1 2/2019
(Continued)

OTHER PUBLICATIONS

CircAid JuxtaFit Essentials arm sleeve by Medi; http://mediusa.com/portfolio-item/juxtafit-essentials-upper-extremity/; Mar. 29, 2015.
(Continued)

*Primary Examiner* — Ophelia A Hawthorne
(74) *Attorney, Agent, or Firm* — FisherBroyles LLP; Anthony Dovale

(57) ABSTRACT

A compression garment includes a spacer fabric part (1) with an inner layer (2) and an outer layer. The compression garment further includes a closing part (4) with at least one macroscopic hook (5). If a user dons the compression garment, the spacer fabric part (1) and/or the closing part (4) has to be stretched to generate the compression force and the stretching is maintained by attaching the closing part (4) to the spacer fabric part (1) by hooking the at least one macroscopic hook (5) into the mesh of the outer layer of the spacer fabric part (1).

18 Claims, 2 Drawing Sheets

(51) Int. Cl.
*A61F 13/06* (2006.01)
*A61L 15/14* (2006.01)

(58) Field of Classification Search
CPC .......... A61F 2013/00119; A61F 13/108; A61F 15/006; A61F 2013/00174; A61F 2013/00468; A61F 13/00008; A61F 13/022; A61F 2013/00957; A61F 5/37; A61F 2013/00131; A61F 13/062; A61F 15/004; A61F 13/0269; A61F 2013/00565; A61F 2013/00093; A61F 13/00029; A61F 13/00034; A61F 13/0226; A61F 13/066; A61F 13/533; A61F 13/55185; A61F 13/62; A61F 2007/0231; A61F 2013/00123; A61F 2013/00604; A61F 2013/00765; A41B 11/00; A41B 11/002; A41B 11/001; A41B 11/02
See application file for complete search history.

(56) References Cited

U.S. PATENT DOCUMENTS

| | | | |
|---|---|---|---|
| 3,856,008 A | 12/1974 | Fowler et al. | |
| D234,271 S | 2/1975 | Moore | |
| 4,215,687 A | 8/1980 | Shaw | |
| 4,367,733 A | 1/1983 | Stromgren | |
| D269,816 S | 7/1983 | Meier et al. | |
| 4,476,857 A | 10/1984 | Levine | |
| 5,108,455 A | 4/1992 | Telikicherla | |
| 5,254,122 A | 10/1993 | Shaw | |
| D353,005 S | 11/1994 | Glidden | |
| 5,385,036 A * | 1/1995 | Spillane | A43B 1/04 2/16 |
| D382,344 S | 8/1997 | Swedberg et al. | |
| 5,904,145 A | 5/1999 | Reid | |
| 5,906,206 A | 5/1999 | Shaw et al. | |
| 6,152,893 A | 11/2000 | Pigg et al. | |
| 6,196,231 B1 | 3/2001 | Reid | |
| 6,254,554 B1 | 7/2001 | Turtzo | |
| 6,338,723 B1 | 1/2002 | Carpenter et al. | |
| 6,516,804 B1 | 2/2003 | Hoffman | |
| 7,329,232 B2 | 2/2008 | Lipshaw et al. | |
| 8,801,645 B2 | 8/2014 | Lipshaw et al. | |
| D717,453 S | 11/2014 | Mahtani | |
| D728,804 S | 5/2015 | Hansen | |
| 9,364,701 B2 | 6/2016 | Bartsch | |
| 9,642,559 B2 | 5/2017 | Falconio-West et al. | |
| 9,642,766 B2 | 5/2017 | Lipshaw et al. | |
| D800,325 S | 10/2017 | Cox | |
| 10,194,755 B1 * | 2/2019 | Flannery | A47D 13/063 |
| D848,625 S | 5/2019 | Chase et al. | |
| D850,632 S | 6/2019 | Chiang et al. | |
| D872,286 S | 1/2020 | Hoffman et al. | |
| 2002/0062096 A1 | 5/2002 | Bennett | |
| 2005/0113729 A1 | 5/2005 | Scott et al. | |
| 2005/0148917 A1 | 7/2005 | Nathanson | |
| 2005/0192524 A1 | 9/2005 | Lipshaw et al. | |
| 2005/0251073 A1 * | 11/2005 | Roth | A61F 5/30 602/8 |
| 2006/0201032 A1 | 9/2006 | Ramsey | |
| 2007/0179421 A1 | 8/2007 | Farrow | |
| 2010/0269240 A1 | 10/2010 | Weir et al. | |
| 2010/0312160 A1 | 12/2010 | Creighton et al. | |
| 2011/0125183 A1 | 5/2011 | Lipshaw et al. | |
| 2011/0185508 A1 | 8/2011 | Hsu et al. | |
| 2011/0257575 A1 | 10/2011 | Farrow et al. | |
| 2012/0179084 A1 | 7/2012 | Lipshaw et al. | |
| 2012/0277073 A1 | 11/2012 | Bartsch | |
| 2013/0283500 A1 | 10/2013 | Lipshaw et al. | |
| 2013/0319128 A1 | 12/2013 | Richardson et al. | |
| 2015/0025424 A1 * | 1/2015 | Richardson | A61H 1/008 601/84 |
| 2016/0000612 A1 | 1/2016 | Cox | |
| 2016/0030251 A1 | 2/2016 | Schuren et al. | |
| 2016/0030267 A1 | 2/2016 | Lipshaw et al. | |
| 2016/0100988 A1 | 4/2016 | Vee et al. | |
| 2016/0166458 A9 | 6/2016 | Lipshaw et al. | |
| 2017/0246024 A1 * | 8/2017 | Vogele | A61B 90/39 |
| 2017/0258672 A1 | 9/2017 | Wennen et al. | |
| 2017/0273830 A1 * | 9/2017 | Hitschmann | A61F 13/00038 |
| 2018/0243143 A1 | 8/2018 | Karadsheh | |
| 2018/0344532 A1 | 12/2018 | Karadsheh et al. | |
| 2019/0133229 A1 | 5/2019 | Hoffman et al. | |
| 2019/0209387 A1 | 7/2019 | Ganzoni | |

FOREIGN PATENT DOCUMENTS

| | | | |
|---|---|---|---|
| AU | 2017329458 A1 | 2/2019 | |
| AU | 2018223706 A1 | 8/2019 | |
| BR | 112019002388 A2 | 6/2019 | |
| BR | 112019002399 A2 | 6/2019 | |
| CA | 2 722 146 A1 | 10/2009 | |
| CA | 3 037 413 A1 | 3/2018 | |
| CA | 3 037 417 A1 | 3/2018 | |
| CA | 3 054 339 A1 | 8/2018 | |
| CH | 712 938 A1 | 3/2018 | |
| CH | 712 939 A1 | 3/2018 | |
| EP | 1052319 A1 | 11/2000 | |
| EP | 1052319 A1 * | 11/2000 | A61F 13/061 |
| EP | 1959880 A1 | 8/2008 | |
| EP | 3 512 478 A1 | 7/2019 | |
| EP | 3 512 479 A1 | 7/2019 | |
| EP | 3 565 515 A1 | 11/2019 | |
| FR | 2 961 389 A1 | 12/2011 | |
| MX | 2019001588 A | 9/2019 | |
| MX | 2019001642 A | 9/2019 | |
| MX | 2019009113 A | 9/2019 | |
| WO | 95/16416 A1 | 6/1995 | |
| WO | 99/30607 A2 | 6/1999 | |
| WO | 00/15139 A2 | 3/2000 | |
| WO | 01/89410 A2 | 11/2001 | |
| WO | 2005/052235 A1 | 6/2005 | |
| WO | 2013/085445 A1 | 6/2013 | |
| WO | 2013/138394 A1 | 9/2013 | |
| WO | 2014/116497 A1 | 7/2014 | |
| WO | 2014/160572 A1 | 10/2014 | |
| WO | 2015/188158 A2 | 12/2015 | |
| WO | 2016048827 A1 | 3/2016 | |
| WO | 2016/105213 A1 | 6/2016 | |
| WO | 2018/054681 A1 | 3/2018 | |
| WO | 2018054682 A1 | 3/2018 | |
| WO | 2018/153611 A1 | 8/2018 | |
| WO | 2019/091811 A1 | 5/2019 | |

OTHER PUBLICATIONS

CircAid Arm Reduction Kit by Medi; http://mediusa.com/portfolio-item/circaid-reduction-kit/; May 20, 2016.
Solaris ReadyWrap arm sleeve by Lohmann & Rauscher; http://www.lymphedemaproducts.com/products/readywrap-arm.html; May 4, 2017.
Solaris TributeWrap Wrist to Axilla; https://www.lohmann-rauscher.com/us-en/products/solaris-collection-by-lr/tributewrap/; date unknown, at least prior to applicant's filing date of Feb. 1, 2018.
FarrowWrap LITE OTS Armpiece by Jobst; http://www.jobst-usa.com/product/jobst-farrow-ots-armsleeve/; Jul. 14, 2017.
FarrowWrap LITE Trim-To-Fit Armpiece by Jobst; http://www.jobst-usa.com/product/jobst-farrowwrap-lite-armpiece/; Jul. 14, 2017.
FarrowWrap Classic Custom Armpiece by Jobst; http://www.jobst-usa.com/product/jobst-farrowwrap-classic-armpiece/; Jul. 18, 2018.
Juzo Arm Compression Wrap; http://www.juzousa.com/Products/Product-Detail?ID=70; date unknown, at least prior to applicant's filing date of Feb. 1, 2018.
MedAssist ArmAssist by SIGVARIS; http://www.lymphedemaproducts.com/products/medassist-armassist.html; at least as of Oct. 17, 2017.
MedaFit Arm by SIGVARIS; https://www.sigvaris.com/usa/en-us/product/medafit; at least as of Jun. 10, 2017.
CompreSleeve Arm by SIGVARIS; https://www.sigvaris.com/usa/en-us/product/compresleeve; at least as of Jun. 10, 2017.

(56) References Cited

OTHER PUBLICATIONS

Notice of Allowance received for U.S. Appl. No. 29/635,709 dated Sep. 5, 2019, 18 pages.
International Search Report for International Application No. PCT/EP2018/051917 dated Mar. 12, 2018.
Non-Final Office Action received for U.S. Appl. No. 15/443,308 dated May 31, 2019, 28 pages.
Non-Final Office Action received for U.S. Appl. No. 15/443,308 dated Nov. 18, 2019, 17 pages.
Non-Final Office Action received for U.S. Appl. No. 15/808,092 dated Jan. 10, 2020, 32 pages.
International Search Report and Written Opinion received for PCT Application Serial No. PCT/US2019/045792 dated Oct. 28, 2019, 8 pages.
International Preliminary Report on Patentability received for PCT Application Serial No. PCT/EP2018/051917 dated Jun. 5, 2019, 10 pages.
International Search Report and Written Opinion received for PCT Application Serial No. PCT/EP2018/079569 dated Feb. 4, 2019, 8 pages.
International Preliminary Report on Patentability received for PCT Application Serial No. PCT/EP2017/072211 dated Apr. 4, 2019, 16 pages.
International Preliminary Report on Patentability received for PCT Application Serial No. PCT/EP2017/072213 dated Apr. 4, 2019, 8 pages.
International Search Report and Written Opinion issued in corresponding International Application PCT/EP2017/072211 dated Feb. 1, 2018.
International Search Report and Written Opinion issued in corresponding International Application No. PCT/EP2017/072213 dated Nov. 10, 2017.

* cited by examiner

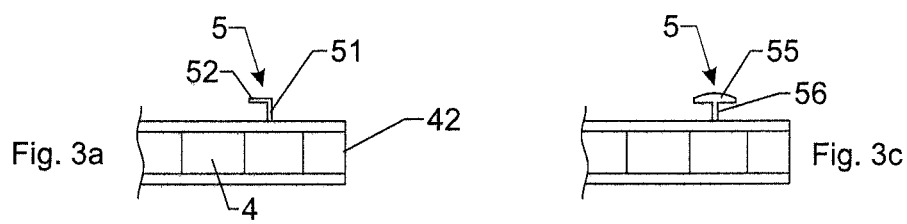
Fig. 3a  Fig. 3c
Fig. 3b  Fig. 3d
Fig. 4
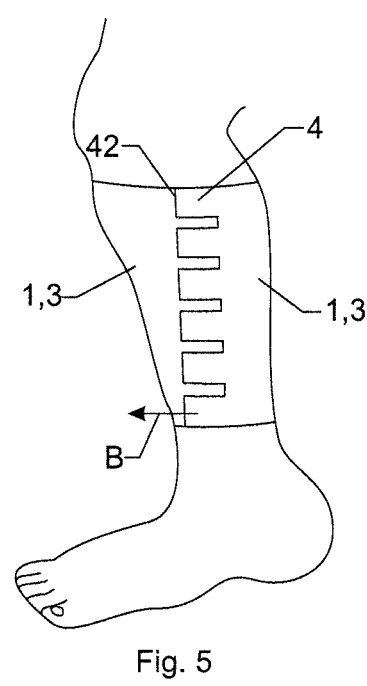
Fig. 5

COMPRESSION GARMENT COMPRISING SPACER FABRIC AND HOOK FASTENER

TECHNICAL FIELD

The present invention relates to a compression garment, in particular stockings or a bandage, for applying compression to a body part.

BACKGROUND ART

Compression garments are used to provide a pressure or a compressive force, respectively, to a human body part, especially to a limb such as an arm or a leg for e.g. the treatment of venous diseases and lymphatic disorders. Medical compression garments are elastic or inelastic garments that can, for example, be used to compress a lower leg, an entire leg, an arm, a hand and so on. They can be designed as stockings, socks, panties, arm sleeves, gloves etc.

Many patients do not wear their compression garments due to difficulties in donning the garment and in dosing the compression force. For an easier donning, compression garments comprising hook-and-loop fasteners (known as Velcro) that are wrapped around a patient's body part are used as an alternative. Hook-and-loop fasteners have typically two strips which are mutually attached to be fastened. One component has microscopic hooks which catch the loops of the other component.

Due to the two component fastening system, the hook component can only be attached where a loop component is arranged on the compression garment. To fit the limbs of most patients, many garments have an additional layer on the whole outer surface that is hook compatible. The breathability of the compression garment is considerably reduced due to the loop compatible layer, reducing the comfort to the wearer of the garment accordingly.

DISCLOSURE OF THE INVENTION

The object of the present invention is to provide a compression garment with an improved closure system.

In order to meet this object, the invention introduces a compression garment according to the independent claim 1.

The compression garment comprises a spacer fabric part. The spacer fabric part is built so that it has an inner layer and an outer layer which are connected such that a distance between the layers is defined. The inner and outer layer are preferably connected by threads and in particular by spacer yarns. The outer layer is a mesh with openings. Furthermore, the compression garment comprises at least one closing part with at least one macroscopic hook. The at least one closing part is attachable by hooking the at least one macroscopic hook into the mesh of the outer layer of the spacer fabric part. Thus, the compression garment, in particular the spacer fabric part and/or the closing parts, can be stretched and the compression garment can be wrapped around the body part and can be fixed by the at least one closing part such that a desired compression force is applied to the body part.

As said, the spacer fabric is a three-dimensional fabric with two knitted layers, the inner layer and the outer layer, which are joined together by spacer yarns.

The preferred yarn types are synthetic such as polyester or polyamide, other yarn types may be used, as well. The spacer fabric is preferably warp-knitted or weft-knitted.

While the inner layer is intended to face the skin, the outer layer has openings to attach to the closing part by the at least one macroscopic hook. In other words, the openings of the outer layer mesh serve as eyelets for the hooks.

A macroscopic hook is understood to be a hook which is recognized in its functioning as one single hook which can be used to fix the closing part. In other words, the hook is visible as such by the naked eye. In contrast to that, the prior art garment with the hook-and-loop fastener has in fact microscopic hooks and in a macroscopic view it functions like an adhesive tape which can be attached by pressing the hook component to the loop component and not by hooking hooks into openings.

The garment according to the invention has the advantage that the closing part with hooks can be attached everywhere on the spacer fabric part. No additional loop components are required. Furthermore, the openings of the spacer fabric part provide a good breathability even where the hooks are attached.

While lint can be trapped between microscopic hooks and make the hook-and-loop fastener inoperable, this problem does not occur with macroscopic hooks.

In a preferred embodiment the openings may be treated with the thermal process called "heat setting", which gives dimensional stability to the spacer fabrics. This prevents tearing or abrasion of the spacer fabric.

It is further preferred that the openings have a size such that a ball with a diameter of 0.5 mm, in particular 1 mm, in particular 1.5 mm, in particular 2 mm, in particular 2.5 mm, in particular 3 mm passes through such an opening.

Openings with certain diameters have the advantage that the hooks can hook into the openings and do not destroy the spacer fabric by tearing the yarns.

In another preferred embodiment the openings have a size such that only a ball with a diameter of less than 4 mm, in particular less than 3 mm, in particular less than 2 mm, in particular less than 1 mm passes through such an opening.

While the openings should not be too small such that the hooks can be hooked into the openings, the openings should not be too large in order to guarantee a high compression force when the garment is wrapped around the body part.

Furthermore, the inner layer of the spacer fabric part, which faces the skin if donned, has preferably such a high mesh density and the at least one macroscopic hook is preferably shaped such that the hook will not penetrate the inner layer upon hooking the hook to the mesh if the compression garment is donned as intended, so that the inner layer functions as a closed surface thanks to its high mesh density.

This has the advantage that the wearer's skin is protected by the inner layer from being irritated by the hooks because the hooks cannot rub the skin if the body part is moved. Furthermore, the thickness of the whole spacer fabric part protects the skin from being irritated by the hooks. The inner layer has a high mesh density and/or the spacer fabric part has a high thickness of at least 2 mm, and the at least one macroscopic hook is shaped such that the at least one macroscopic hook cannot penetrate the inner layer upon hooking the macroscopic hook into the mesh of the outer layer.

In a further preferred embodiment the at least one hook is made of metal. Since only a few hooks transmit the forces caused by the stretched garment, the hooks need to have a certain stiffness in order to not deform. As an alternative, hooks made of a plastic material may be used.

In another preferred embodiment the at least one hook has an L-form such that one L-element is approximately perpendicular to and the other L-element is approximately parallel to the outer layer of the spacer fabric part. Such hooks have already been used as a closure part of bras. Hooks of this shape can be easy to detach and therefore preferred for a garment that is frequently opened.

A further preferred embodiment is a compression garment wherein the at least one hook has a T-form with a T-stem and a T-crossbar such that the T-stem is approximately perpendicular to and the T-crossbar is approximately parallel to the outer layer of the spacer fabric part.

A T-form has the advantage that the closure part cannot easily be pulled out of the spacer fabric part by movements of the body part. Hooks of this shape can be less easy to detach and may be used for garments which are less frequently opened.

Furthermore the at least one hook can have a mushroom-shape with a mushroom-stem and a mushroom head.

In another preferred embodiment the at least one hook has a single part that is set at an acute angle to the outer layer of the spacer fabric part if hooked in. An "acute angle" is less than 90°.

Furthermore the spacer fabric part can fully surround the body part to be compressed. This has the advantage that a homogenous compression can be applied to the whole body part.

Other advantageous embodiments are listed in the dependent claims as well as in the description below.

BRIEF DESCRIPTION OF THE DRAWINGS

The above and other features and advantages of the present invention will become more apparent to those of ordinary skill in the art by describing in detail preferred embodiments thereof with reference to the attached drawings in which:

FIGS. 3a to 3d illustrate four different variants of hooks which are compatible to be attached to the spacer fabric part;

FIG. 4 is a detailed view of an example embodiment, wherein the closing part with the hooks is attached to the spacer fabric part; and FIG. 5 illustrates an example embodiment of the disclosed invention, wherein the compression garment is donned at the lower leg of the user.

MODES FOR CARRYING OUT THE INVENTION

Figure 1:
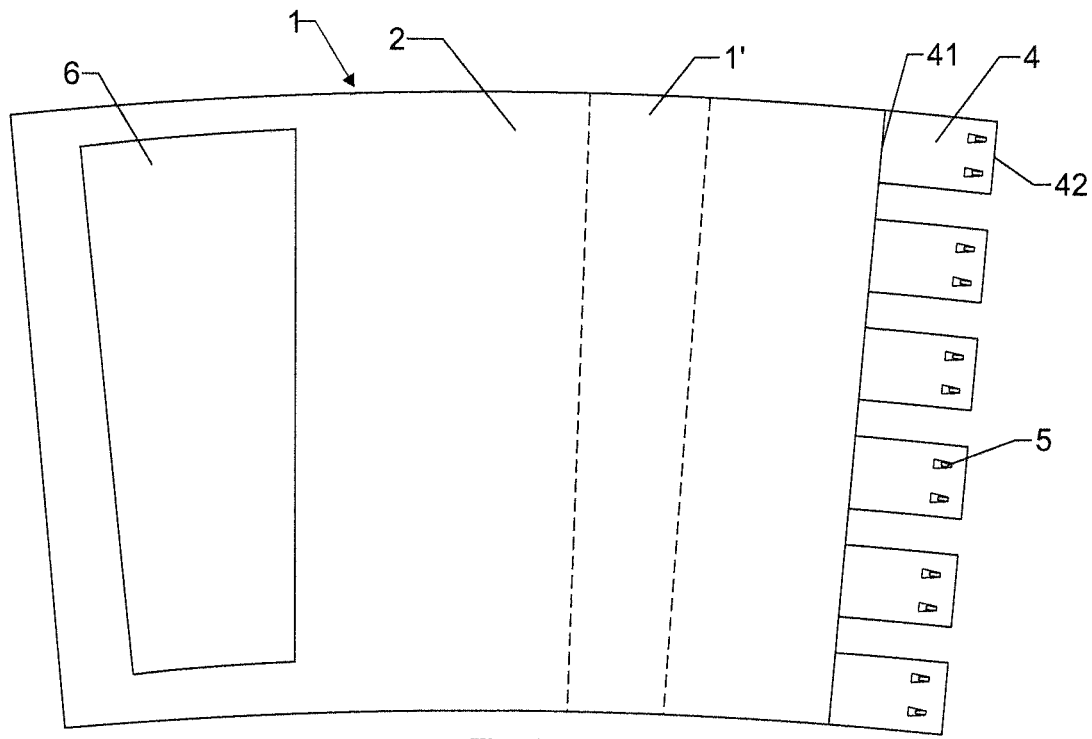
FIG. 1 illustrates an example embodiment of the disclosed compression garment with six closing parts, wherein each closing part comprises two hooks.

FIG. 1 illustrates a compression garment which is adapted to be wrapped around a leg and thus is generally of a bandage-like shape. The garment comprises a spacer fabric part 1 which is fully made of spacer fabric. FIG. 1 shows a view directed to the inner layer 2 of the spacer fabric part 1. This inner layer 2 is intended to face the skin of the user if donned.

Spacer fabric is a stretchable material which can be stretched such that the leg is compressed by the compression garment if donned. Preferably, the spacer fabric has only little stretchability of less than 10%.

An insert 1' or several inserts 1' may be provided in such a garment which are made of a material different than a spacer fabric and having a greater stretchability than the spacer fabric.

Furthermore, the compression garment of this example embodiment comprises six closing parts 4, wherein each closing part comprises two hooks 5. The closing parts 4 can be made of the same material as the spacer fabric part 1 or in particular they can be made of a more stretchable material. The closing parts 4 have an inner end 41, which is connected to the spacer fabric part 1, and an outer end 42.

The example embodiment may comprise a donning aid. In this case it is a stretchable sleeve 6 with a small compression force, such that it can easily be donned. After having pulled the sleeve over the leg, the user wraps the spacer fabric part 1 around the leg, stretches the spacer fabric part 1 and the closing parts 4 and attaches the closing parts 4 to the outer layer 3 of the spacer fabric part 1 to maintain the stretching and the compression force.

Figure 2A:
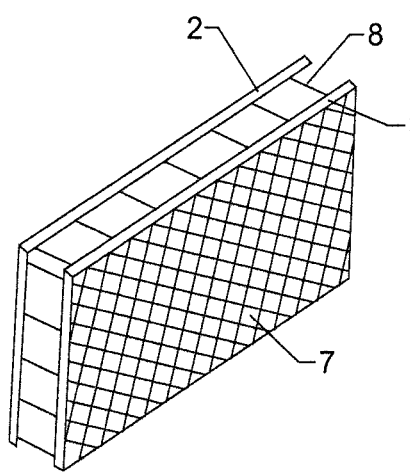
FIGS. 2a and 2b are detailed views of the spacer fabric part.
Figure 2B:
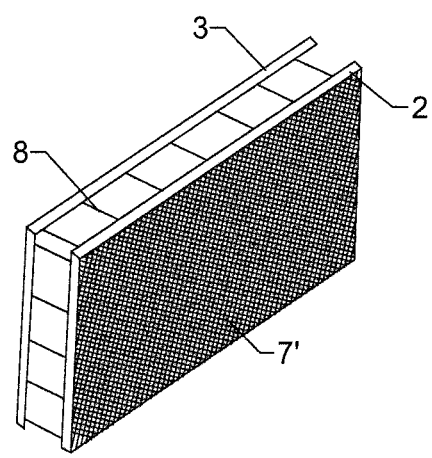

FIGS. 2a and 2b illustrate a segment of the spacer fabric part 1 of the compression garment. FIG. 2a shows a view with the outer layer 3 in front and FIG. 2b shows a view with the inner layer 2 in front. The outer layer 3 has a mesh with larger openings 7 than the mesh openings 7' of the inner layer 2. The openings 7 of the outer layer 3 are sized so large that the hooks 5 of the closing part 4 can be hooked into them. The inner layer 2, which is intended to face the skin of the user if donned, is provided with openings sized so small that the hooks 5 cannot pass them. Therefore, the skin is protected from injuries or skin irritations that may otherwise be caused by the hooks 5. The inner layer 2 and the outer layer 3 are joined together by spacer yarns 8.

FIGS. 3a to 3d illustrate different types of hooks 5 provided on the closing parts 4. The closing parts 4 can be made of the same material as the spacer fabric part 1 or in particular they can be made of a more stretchable material. FIG. 3a shows a hook 5 which has an L-form. One L-element 51 is approximately perpendicular to and the other L-element 52 is approximately parallel to the outer layer of the spacer fabric part 1 if the closing part 4 is attached to the spacer fabric part 1. In this case the closing part 4 is made of spacer fabric like the spacer fabric part, as an example.

FIG. 3b illustrates a hook 5 with a T-form such that the T-stem 54 is approximately perpendicular to and the T-crossbar 53 is approximately parallel to the outer layer of the spacer fabric if hooked into the mesh of the spacer fabric.

In a further example embodiment the hook 5 has a mushroom-shape with a mushroom-stem 56 and a mushroom-head 55, as shown in FIG. 3c.

FIG. 3d illustrates a very simple hook 5 having one single angled part 57 arranged at the closing part 4.

FIG. 4 shows a detailed view of the compression garment wherein the closing parts 4 are attached to the spacer fabric part 1 by hooking the hooks 5 into the mesh of the outer layer 2 of the spacer fabric part 1. The hook 5 of the closing part 4 has an L-form. It is passed through an opening 7 of the outer layer 3 of the spacer fabric part 1. If the closing part 4 is attached to the spacer fabric part 1, one L-element 51 is arranged perpendicular to the outer layer 3 of the spacer fabric part 1 and the other L-element 52 is arranged in parallel to the outer layer 3 of the spacer fabric part 1. If the compression garment is correctly donned by wrapping the garment around the patient's body part and the closing parts 4 are attached, the spacer fabric part 1 and the closing parts 4 are stretched to compress the body part such that the closing parts 4 are pulled in the direction A. Therefore, the perpendicularly arranged L-element 51 attaches to an edge of the opening 7. The pulling direction A is directed to the opposite side of the outer end 42 of the closing part 4.

FIG. 5 illustrates a compression garment that has been donned at a lower leg of a user. The spacer fabric part 1 fully surrounds the body part to be compressed. The closing parts 4 are attached to the spacer fabric part 1 by hooking the hooks 5 into the mesh of the outer layer 3. This Figure shows the garment to close on the medial side of the leg but of course the garment can be arranged as well to be suitable to close on the lateral side of the leg.

The compression garment can be taken off by pulling the closing parts 4 in the direction shown by the arrow B until the hooks 5 can be pulled out through the openings of the outer layer 3.

Thus a compression garment comprises a spacer fabric part 1 with an inner layer 2 and an outer layer 3. The compression garment further comprises a closing part 4 with at least one macroscopic hook 5. If a user dons the compression garment, the spacer fabric part 1 and the closing parts 4 have to be stretched to generate the compression force and the stretched spacer fabric part 1 is fixed by attaching the closing part 4 to the spacer fabric part 1 by hooking the macroscopic hook 5 into an opening 7 of the mesh of the outer layer 3 of the spacer fabric part 1.

The invention claimed is:

1. A compression garment sized to be wrapped around a patient's body part for applying compression to the body part, the compression garment comprising:
    a spacer fabric part and wherein the spacer fabric part has an inner layer and an outer layer,
    the outer layer is a mesh with openings; and
    at least one closing part having at least one macroscopic hook, wherein the at least one closing part is attachable by hooking the at least one macroscopic hook into the mesh of the outer layer of the spacer fabric part, and the at least one macroscopic hook is shaped such that the at least one macroscopic hook cannot penetrate the inner layer upon hooking the macroscopic hook into the mesh of the outer layer.

2. A compression garment according to claim 1 wherein the spacer fabric part is a three-dimensional fabric with two knitted layers, the inner layer and the outer layer, which are joined together by spacer yarns,
    in particular wherein the spacer fabric part is made of a synthetic yarn, in particular made of polyester or polyamide, in particular wherein the spacer fabric part is warp-knitted or weft-knitted.

3. A compression garment according claim 1, wherein the openings are heat setted.

4. A compression garment according to claim 1, wherein the openings have a size such that a ball with a diameter of 0.5 mm to 3 mm passes through an opening of the openings.

5. A compression garment according to claim 1, wherein the openings have a size such that only a ball with a diameter of less than 4 mm passes through an opening of the openings.

6. A compression garment according to claim 1, wherein the inner layer has a high mesh density and/or the spacer fabric part has a high thickness of at least 2 mm.

7. A compression garment according to claim 1, wherein the inner layer has a high mesh density that the at least one macroscopic hook is hooked in between the outer layer and the inner layer.

8. A compression garment according to claim 1, wherein the at least one macroscopic hook is made of metal or wherein the at least one macroscopic hook is made of a plastic material.

9. A compression garment according to claim 1, wherein the at least one macroscopic hook has an L-form such that one L-element is approximately perpendicular to and the other L-element is approximately parallel to the outer layer of the spacer fabric part when hooked in.

10. A compression garment according to claim 1, wherein the at least one macroscopic hook has a T-form with a T-stem and a T-crossbar such that the T-stem is approximately perpendicular to and the T-crossbar is approximately parallel to the outer layer of the spacer fabric part when hooked in.

11. A compression garment according to claim 1, wherein the at least one macroscopic hook has a mushroom-shape with a mushroom-stem and a mushroom head.

12. A compression garment according to claim 1, wherein the at least one macroscopic hook has a single part that is set at an acute angle to the outer layer of the spacer fabric part when hooked in.

13. A compression garment according to claim 1, wherein the spacer fabric part is sized such that after wrapping it fully surrounds the body part to be compressed.

14. A compression garment according to claim 1, wherein the compression garment comprises a donning aid, in particular a stretchable sleeve, provided on the inner layer of the spacer fabric part.

15. A compression garment according to claim 1, wherein the openings of the outer layer mesh serve as eyelets for the at least one macroscopic hook.

16. A compression garment according to claim 1, wherein the at least one closing part is attachable by hooking the at least one macroscopic hook into at least one of the openings of the mesh of the outer layer of the spacer fabric part.

17. A method of donning a compression garment comprising:
    wrapping the compression garment around a patient's body part for applying compression to such body part, said garment comprising:
        a spacer fabric part and said spacer fabric part having an inner layer and an outer layer, wherein the outer layer is a mesh with openings, and
        at least one closing part having at least one macroscopic hook, wherein the at least one closing part is attachable to the outer layer;
    hooking the at least one macroscopic hook into the mesh of the outer layer of the spacer fabric part to apply a desired compression level to the body part by stretching the compression garment and fixing the at least one closing part by the at least one macroscopic hook, and the at least one macroscopic hook is shaped such that the at least one macroscopic hook cannot penetrate the inner layer upon hooking the macroscopic hook into the mesh of the outer layer.

18. A method according to claim 17, wherein the at least one closing part is attachable by hooking the at least one macroscopic hook into one of the openings of the mesh of the outer layer of the spacer fabric part to apply a desired compression level to the body part by:
    stretching the compression garment; and
    fixing the at least one closing part by the at least one macroscopic hook.

* * * * *